US009046496B2

(12) United States Patent  
Tsai et al.

(10) Patent No.: US 9,046,496 B2  
(45) Date of Patent: Jun. 2, 2015

(54) CAPTURING METHOD FOR IMAGES WITH DIFFERENT VIEW-ANGLES AND CAPTURING SYSTEM USING THE SAME

(75) Inventors: Ya-Hui Tsai, Pingjhen (TW); Kuo-Tang Huang, Pingjhen (TW); Chin-Kuei Chang, New Taipei (TW); Chun-Lung Chang, Zhubei (TW)

(73) Assignee: Industrial Technology Research Institute, Hsinchu (TW)

( * ) Notice: Subject to any disclaimer, the term of this patent is extended or adjusted under 35 U.S.C. 154(b) by 318 days.

(21) Appl. No.: 13/371,060

(22) Filed: Feb. 10, 2012

(65) Prior Publication Data

US 2012/0249753 A1 Oct. 4, 2012

Related U.S. Application Data

(60) Provisional application No. 61/468,590, filed on Mar. 29, 2011.

(30) Foreign Application Priority Data

Aug. 15, 2011 (TW) .............................. 100129124 A

(51) Int. Cl.  
*H04N 13/02* (2006.01)  
*H04N 13/00* (2006.01)  
(Continued)

(52) U.S. Cl.  
CPC .......... *G01N 21/8806* (2013.01); *G01N 21/956* (2013.01); *G01N 2021/8835* (2013.01); *G01N 2021/95638* (2013.01)

(58) Field of Classification Search  
None  
See application file for complete search history.

(56) References Cited

U.S. PATENT DOCUMENTS 7,420,542 B2 9/2008 Butterworth et al.  
2007/0211240 A1* 9/2007 Matsumoto et al. ....... 356/237.1  
(Continued)

FOREIGN PATENT DOCUMENTS

CN 101004389 7/2007  
CN 201212653 A 7/2008  
(Continued)

OTHER PUBLICATIONS

Tsai, et al., Research Article, "Surface Defect Detection of 3D Objects Using Robot Vision", *Industrial Robot: An International Journal*, vol. 38, No. 4, 2011, pp. 381-398.  
(Continued)

*Primary Examiner* — Jorge L Ortiz Criado  
*Assistant Examiner* — Samuel D Fereja  
(74) *Attorney, Agent, or Firm* — Muncy, Geissler, Olds & Lowe, P.C.

(57) ABSTRACT

A capturing method for a plurality of images with different view-angles and a capturing system using the same are provided. The capturing method for the images with different view-angles includes the following steps. An appearance image of an object is captured by an image capturing unit at a capturing angle. A light reflection area of the appearance image is detected by a detecting unit, and a dimension characteristic of the light reflection area is analyzed by the same. Whether the dimension characteristic of the light reflection area is larger than a first predetermined value is determined. If the dimension characteristic of the light reflection area is larger than the first predetermined value, then the capturing angle is adjusted within a first adjusting range. After the step of adjusting the capturing angle within a first adjusting range is performed, the step of capturing the appearance image is performed again.

19 Claims, 6 Drawing Sheets

(51) Int. Cl.
*G01N 21/88* (2006.01)
*G01N 21/956* (2006.01)

(56) References Cited

U.S. PATENT DOCUMENTS

| | | | |
|---|---|---|---|
| 2008/0030744 A1* | 2/2008 | Beardsley | 356/601 |
| 2009/0179910 A1* | 7/2009 | Inoue et al. | 345/581 |
| 2009/0231145 A1* | 9/2009 | Wada et al. | 340/575 |
| 2010/0091272 A1* | 4/2010 | Asada et al. | 356/237.2 |
| 2010/0165094 A1* | 7/2010 | Kakuda et al. | 348/92 |
| 2011/0144505 A1* | 6/2011 | Yamamoto et al. | 600/476 |
| 2012/0206710 A1* | 8/2012 | Niemel et al. | 356/4.07 |

FOREIGN PATENT DOCUMENTS

| | | |
|---|---|---|
| CN | 101639452 | 2/2010 |
| CN | 101685001 A | 3/2010 |
| JP | 2008292430 | 4/2008 |
| WO | WO2009044944 | 4/2009 |

OTHER PUBLICATIONS

Song, et al., "Three-Dimensional Measurement and Defect Detection Based on Single Image", *Journal of Optoelectronics and Advanced Materials*, vol. 7, No. 2, Apr. 2005, pp. 1029-1038.

Aluze et al., "Vision system for defect imaging, detection, and characterization on a specular surface of a 3D object" *Image and Vision Computing* 20 (2002) pp. 569-580.

Li et al., "Computer vision based system for apple surface defect detection" *Computers and Electronics in Agriculture* 36 (2002) pp. 215-223.

* cited by examiner

CAPTURING METHOD FOR IMAGES WITH DIFFERENT VIEW-ANGLES AND CAPTURING SYSTEM USING THE SAME

This application claims the benefit of U.S. Provisional application Ser. No. 61/468,590, filed Mar. 29, 2011 and Taiwan application Serial No. 100129124, filed Aug. 15, 2011, the disclosure of which is incorporated by reference herein in its entirety.

BACKGROUND

1. Technical Field

The disclosed embodiments relate in general to a capturing method and a capturing system using the same, and more particularly to a capturing method for a plurality of images with different view-angles and a capturing system using the same.

2. Description of the Related Art

Along with the advance in technology, various electronic devices are provided over the time. For an electronic device, the appearance quality is also highly valued by consumers in addition to the functional performance. Investigation shows that the sale return due to the problem of appearance quality has become a heavy burden to the manufacturers. Thus, before a final product is delivered from the factory, the manufacturers would normally check the important parts and the appearance of the final product.

However, most appearance surfaces of electronic devices are curved or non-uniformed, and would therefore generate reflection or non-uniformity of the light. Due to the capturing angle and the projection of the light source, the light shadow or false appearance formed by electronic devices normally fails to reflect the characteristics of defects. Since the ordinary 2D planar static image detecting device is incapable of detecting the above defects and the 3D appearance detecting device is not yet available, currently, the detection can only be done manually.

To perform 3D surface check on electronic devices, the image must be captured at multiple view-angles. The reflection of the light generated at different view-angles varies accordingly and is difficult to control. Therefore, how to capture an appearance image whose light reflection area is conformed to the requirements at each view-angle has become an imminent task for the industries.

SUMMARY

The disclosure is directed to a capturing method for a plurality of images with different view-angles and a capturing system using the same, which reduce the dimension characteristic of a light reflection area of an appearance image for each view-angle by way of dynamic detection and adjustment.

According to one embodiment, a capturing method for a plurality of images with different view-angles is provided. The capturing method for the images with different view-angles includes the following steps. An appearance image of an object is captured by an image capturing unit at a capturing angle. A light reflection area of the appearance image is detected by a detecting unit, and a dimension characteristic of the light reflection area is analyzed by the same. Whether the dimension characteristic of the light reflection area is larger than a first predetermined value is determined. If the dimension characteristic of the light reflection area is larger than the first predetermined value, then the capturing angle is adjusted within a first adjusting range. After the step of adjusting the capturing angle within a first adjusting range is performed, the step of capturing the appearance image is performed again.

According to another embodiment, a capturing system for capturing a plurality of images with different view-angles is provided. The capturing system includes an image capturing unit, a detecting unit, a determining unit and an adjusting unit. The image capturing unit is used for capturing an appearance image of an object at a capturing angle. The detecting unit is used for detecting a light reflection area of the appearance image, and analyzing a dimension characteristic of the light reflection area. The determining unit is used for determining whether the dimension characteristic of the light reflection area is larger than a first predetermined value. If the dimension characteristic of the light reflection area is larger than the first predetermined value, then the capturing angle is adjusted by the adjusting unit within a first adjusting range. After the adjusting unit adjusts the capturing angle within a first adjusting range, the image capturing unit again captures the appearance image.

The above and other aspects of the disclosure will become better understood with regard to the following detailed description of the non-limiting embodiment(s). The following description is made with reference to the accompanying drawings.

Figure 1:
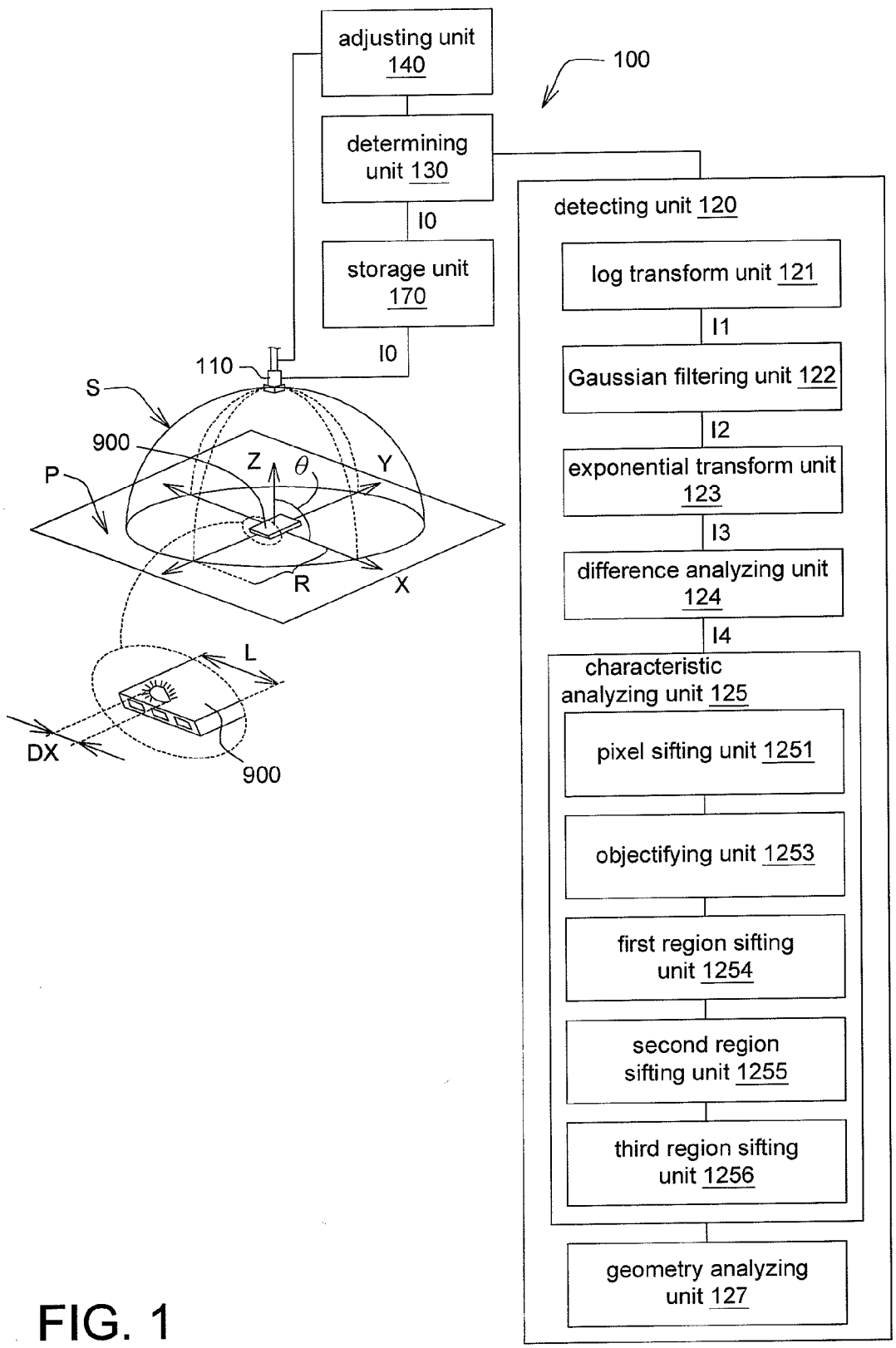
FIG. 1 shows a schematic diagram of a capturing system according to an embodiment of the disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

DETAILED DESCRIPTION

Referring to FIG. 1, a schematic diagram of a capturing system 100 according to an embodiment of the disclosure is shown. The capturing system 100 includes an image capturing unit 110, a detecting unit 120, a determining unit 130, an adjusting unit 140 and a storage unit 170. The image capturing unit 110, used for capturing an image, is realized by such as a camera or a video recorder. The detecting unit 120 is used for detecting a light reflection area of an image. The determining unit 130 is used for executing various determining procedures. The detecting unit 120 and the determining unit 130 are realized by such as a micro-processing chip set, a firmware circuit, or a storage medium storing a plurality of programming codes. The adjusting unit 140 is used for adjusting the position, angle and environment light source of the image capturing unit 110. The storage unit 170, used for storing data, can be realized by such as a hard disc, a memory, a flash drive or a memory card.

In the present embodiment of the disclosure, the image capturing unit 110 can be equipped with a movable mechanism (eye-in-hand) and a dom-shaped light source, wherein the shape of the light source is not limited to a dom, a ring, a square, a quadrilateral or a strip, and the light source for providing supplementary lighting can also be used. The object 900 is disposed on a platform P, and the image capturing system 100 captures a plurality of appearance images I0 with a plurality of view-angles above the object 900 along a X-axial direction and a Y-axial direction of a hemispheric surface S.

A dimension characteristic (such as a ratio of an area measurement, a perimeter, each length of a long axis and a short axis, or a ratio of the long axis to the short axis) of some light reflection areas of the captured appearance images I0 may be too large. Therefore, in the present embodiment of the disclosure, adjustment at each view-angle is performed for reducing the dimension characteristic of some light reflection areas of the appearance images I0 captured at each view-angle to an acceptable range, so that the image can be subsequently used for defecting defects.

Figure 2:
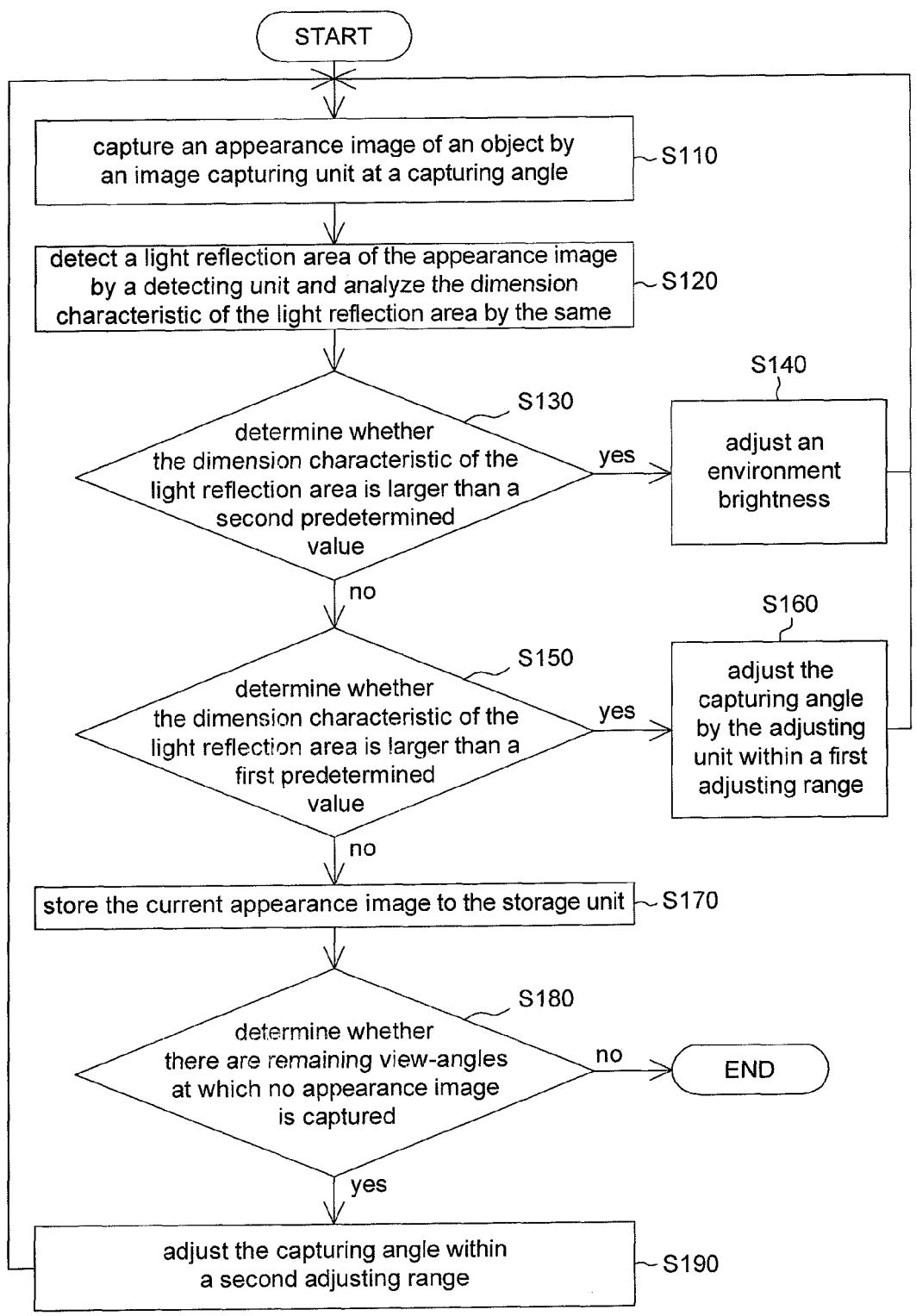
FIG. 2 shows a flowchart of a capturing method according to an embodiment of the disclosure.

Referring to FIG. 2, a flowchart of a capturing method for the images with different view-angles according to an embodiment of the disclosure is shown. The capturing method for the images with different view-angles of the present embodiment of the disclosure is exemplified with the capturing system 100 of FIG. 1. However, anyone who is skilled in the technology of the disclosure will understand that the application of the capturing method for the images with different view-angles of the present embodiment of the disclosure is not limited to the capturing system 100 of FIG. 1, and the application of the capturing system 100 of FIG. 1 is not limited to the capturing method for the images with different view-angles of FIG. 2 either.

In step S110, an appearance image I0 of an object 900 is captured by the image capturing unit 110 at a capturing angle θ. The capturing angle θ such as corresponds to a view-angle on the X axis of the hemispheric surface S. In steps S120 to S160, the capturing angle θ and the brightness of the light source are fine-tuned so that the dimension characteristic of the light reflection area of the appearance image I0 captured at the specific view-angle is reduced to an acceptable range.

Figure 4:
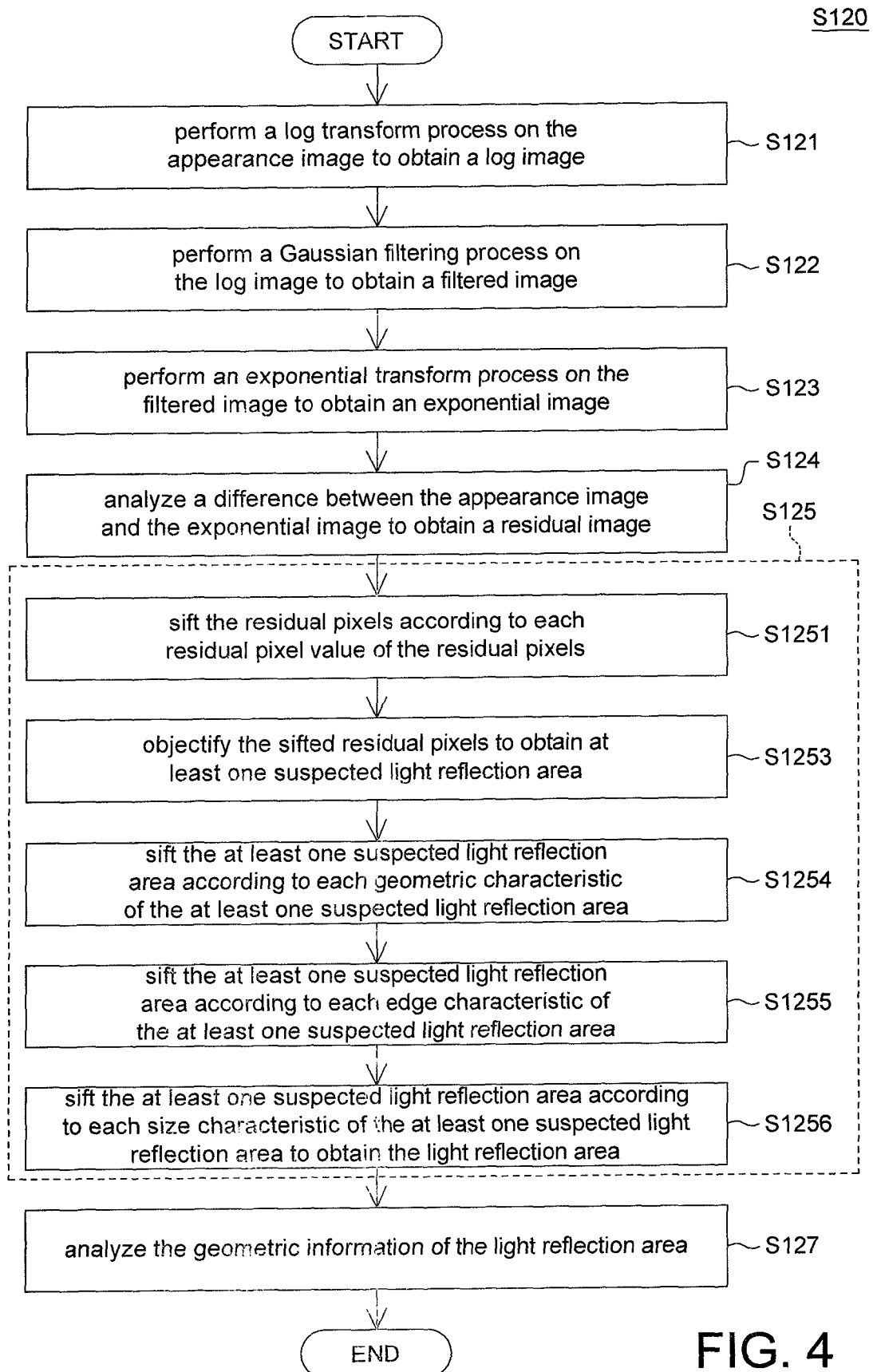
FIG. 4 shows a schematic diagram of the step S120 of FIG. 2 according to an embodiment of the disclosure.

In step S120, a light reflection area of the appearance image I0 is detected by the detecting unit 120, and a dimension characteristic of the light reflection area is analyzed by the same. In the present step, the detecting unit 120 analyzes the appearance image I0 to recognize which portion belongs to the light reflection area. There could be several light reflection areas detected at the beginning. After suitable analysis procedure is performed, a light reflection area with a larger dimension characteristic is sifted. The number of sifted light reflection area can be one (for example, the light reflection area with the largest dimension characteristic is sifted) or several (for example, a plurality of light reflection areas whose dimension characteristic is larger than a threshold are selected). The step S120 includes a plurality of sub-steps as indicated in FIG. 4. Descriptions related to FIG. 4 are given in subsequent paragraphs. In step S120, at least the dimension characteristic of the light reflection area is analyzed. In other embodiments, step S120 may further analyze other geometric information such as the center position, the long axis, the short axis, and the bounding rectangle.

In step S130, whether the dimension characteristic of the light reflection area is larger than a second predetermined value is determined by the determining unit 130. If the dimension characteristic of the light reflection area is larger than the second predetermined value, then the process proceeds to step S140. If the dimension characteristic of the light reflection area is not larger than the second predetermined value, then the process proceeds to step S150.

In step S140, an environment brightness is adjusted by the adjusting unit 140. For example, the brightness of a dom-shaped light source is adjusted, wherein the shape of the light source is not limited to a dom, a ring, a square, a quadrilateral or a strip, and the light source for providing supplementary lighting can also be used. In present step, the dimension characteristic of the light reflection area can be reduced by decreasing the environment brightness.

After step S140 is completed, the process returns to step S110, another appearance image I0 is captured by the image capturing unit 110. That is, steps S110 to S140 will be repeated until the dimension characteristic of the light reflection area is not larger than the second predetermined value, and only then will the method proceed to step S150.

In step S150, whether the dimension characteristic of the light reflection area is larger than a first predetermined value is determined by the determining unit 130. If the dimension characteristic of the light reflection area is larger than the first predetermined value, then the process proceeds to step S160. If the dimension characteristic of the light reflection area is not larger than the first predetermined value, then the process proceeds to step S170. The second predetermined value may be larger than or smaller than the first predetermined value. In the present embodiment of the disclosure, the second predetermined value is smaller than the first predetermined value.

In step S160, the capturing angle θ is adjusted by the adjusting unit 140 within a first adjusting range. The first adjusting range is such as ½, ⅓ or a particular ratio of the length DX of the light reflection area along the X axis. The design of the first adjusting range has much to do with the radius R of the hemispheric surface S, and the smaller the radius R of the hemispheric surface S is, the smaller the first adjusting range will be. In the present step, the adjustment made on the capturing angle θ is very small, and the image capturing unit 110 will not be adjusted to other view-angle.

After step S160 is completed, the process returns to step S110, another appearance image I0 is again captured by the image capturing unit 110. That is, steps S110 to S130 and steps S150 to S160 will be repeated until the dimension characteristic of the light reflection area is not larger than the first predetermined value, and then the process will proceed to step S170. After the process proceeds to step S170, this indicates that the dimension characteristic of the light reflection area is conformed to an acceptable range.

In step S170, the current appearance image I0 is stored to the storage unit 170. Since the dimension characteristic of the light reflection area of the appearance image I0 is already conformed to an acceptable range, the view-angle can be designated by the appearance image I0.

In step S180, whether there are remaining view-angles at which no appearance image I0 is captured is determined by the determining unit 130. If yes, then the process proceeds to step S190. If no, the process terminates.

In step S190, the capturing angle is adjusted by the adjusting unit 140 within a second adjusting range. The second adjusting range is different from the first adjusting range. The second adjusting range can be larger than the first adjusting range. Or, the second adjusting range can be smaller than the first adjusting range. For example, if the length DX of the light reflection area along the X axis is smaller than or a predetermined ratio (such as ⅔) of the length L of the object 900 along the X axis, then the second adjusting range is larger than the first adjusting range. If the length DX of the light reflection area along the X axis is larger than a predetermined ratio (such as ⅔) of the length L of the object 900 along the X axis, then the second adjusting range is smaller than the first adjusting range.

After step S190 is completed, the process returns to step S110, the appearance image I0 along another view-angle is again captured by the image capturing unit 110. That is, steps S110 to S170 are performed again and repeatedly until an appearance image I0 representing the view-angle is obtained.

Through the above process, the appearance image I0 whose light reflection area is conformed to an acceptable range is stored at each view-angle. Despite the above process is exemplified by a plurality of view-angles on the X axis, a plurality of view-angles on the Y axis or other directional axis are also applicable to the above process. The implementations and descriptions for the two applications are similar, and the similarities are not repeated.

Figure 3:
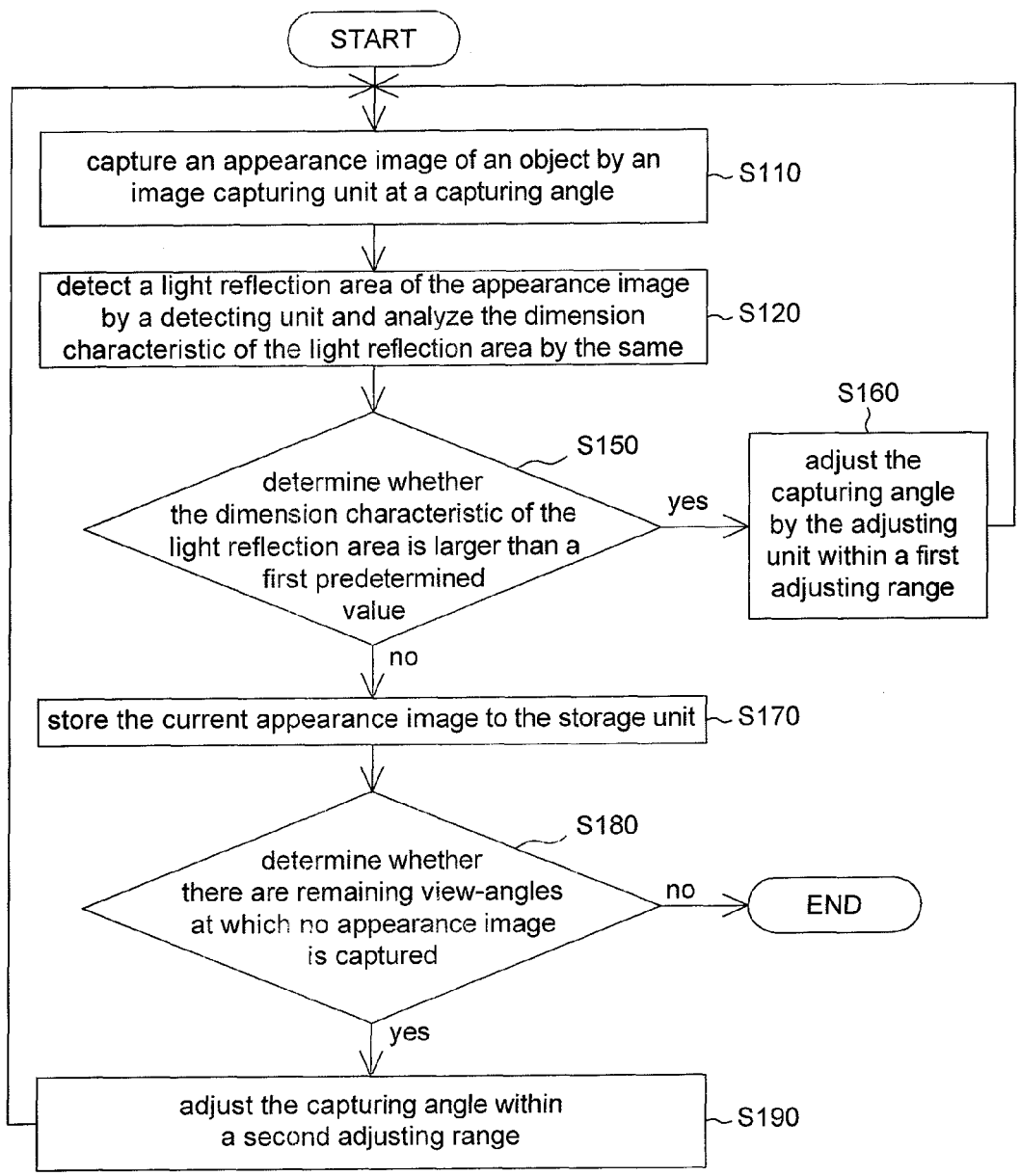
FIG. 3 shows a flowchart of a capturing method according to another embodiment of the disclosure.

Despite the capturing method for the images with different view-angles of the present embodiment of the disclosure is exemplified by the flowchart of FIG. 2, the capturing method for the images with different view-angles of the present disclosure is not limited to such exemplification. Referring to FIG. 3, a flowchart of a capturing method for the images with different view-angles according to another embodiment of the disclosure is shown. In another embodiment, step S130 and step S140 can be omitted, and the process can directly proceed to step S150 after step S120 is completed. Or, step S130 and step S140 can be performed after step S150 and step S160 are completed.

Referring to FIG. 4, a schematic diagram of the step S120 of FIG. 2 according to an embodiment of the disclosure is shown. The step S120 of the present embodiment of the disclosure includes a plurality of sub-steps S121 to S125 and S127. Let the capturing system 100 of FIG. 1 be taken for example. The detecting unit 120 of the capturing system 100 of the present embodiment of the disclosure includes a log transform unit 121, a Gaussian filtering unit 122, an exponential transform unit 123, a difference analyzing unit 124, a characteristic analyzing unit 125 and a geometry analyzing unit 127. The characteristic analyzing unit 125 includes a pixel sifting unit 1251, an objectifying unit 1253, a first region sifting unit 1254, a second region sifting unit 1255 and a third region sifting unit 1256.

In step S121, a log transform process is performed on the appearance image I0 by the log transform unit 121 to obtain a log image I1.

In step S122, a Gaussian filtering process is performed on the log image I1 by the Gaussian filtering unit 122 to obtain a filtered image I2.

In step S123, an exponential transform process is performed on a filtered image I2 by the exponential transform unit 123 to obtain an exponential image I3.

In step S124, a difference between the appearance image I0 and the exponential image I3 is analyzed by the difference analyzing unit 124 to obtain a residual image I4.

In step S125, the light reflection area is obtained by the characteristic analyzing unit 125 according to the residual image I4. In step S125, the residual image I4 includes a plurality of residual pixels. Through steps S1251, and S1253 to S1256, the light reflection area is analyzed according to the residual pixels. In FIG. 4, steps S1254 to S1256 are performed in sequence. In other embodiments, steps S1254 to S1256 can be performed according to other arrangements of sequence, or, only one or two of steps S1254 to S1256 is performed. The number and sequence of steps S1254 to S1256 are determined according to the needs of the design.

In step S1251, residual pixels are sifted by the pixel sifting unit 1251 according to each residual pixel value of the residual pixels. For example, the pixel sifting unit 1251 deletes these residual pixels whose pixel values are smaller than a predetermined threshold, and selects these residual pixels whose pixel values are larger than the threshold. The selected residual pixels are suspected reflective pixels.

In step S1253, the selected residual pixels are objectified by the objectifying unit 1253 to obtain at least one suspected light reflection area. That is, the objectifying unit 1253 connects the selected residual pixels to form a plurality of suspected light reflection areas one by one.

In step S1254, the suspected light reflection areas are sifted by the first region sifting unit 1254 according to the geometric characteristic of the suspected light reflection area. That is, the first region sifting unit 1254 deletes these suspected light reflection areas whose geometric characteristic is significant (the suspected light reflection areas with significant geometric characteristic could be the original pattern of the object 900) but reserves these suspected light reflection areas whose geometric characteristic is insignificant.

In step S1255, the suspected light reflection areas are sifted by the second region sifting unit 1255 according to the edge characteristic of the suspected light reflection area. That is, the second region sifting unit 1255 deletes these suspected light reflection areas whose edge fuzzy degree is lower (the suspected light reflection areas with lower edge fuzzy degree could be the original pattern of the object 900) but reserves these suspected light reflection areas whose edge fuzzy degree is higher. In the present step, the edge fuzzy degree is analyzed according to the pixel values of the original appearance image I0.

In step S1256, the suspected light reflection areas are sifted by the third region sifting unit 1256 according to the dimension characteristic of the suspected light reflection area to obtain the light reflection area. That is, these light reflection areas whose dimension characteristic is larger than a specific threshold can be set by the user or selected from the suspected light reflection areas built in the system, and can be defined as the light reflection areas.

In step S127, the dimension characteristic of the light reflection area, such as the center-of-gravity position or the geometric center position, are analyzed by the geometry analyzing unit 127. The dimension characteristic obtained from analysis can be used in step S130 or step S150.

Figure 5:
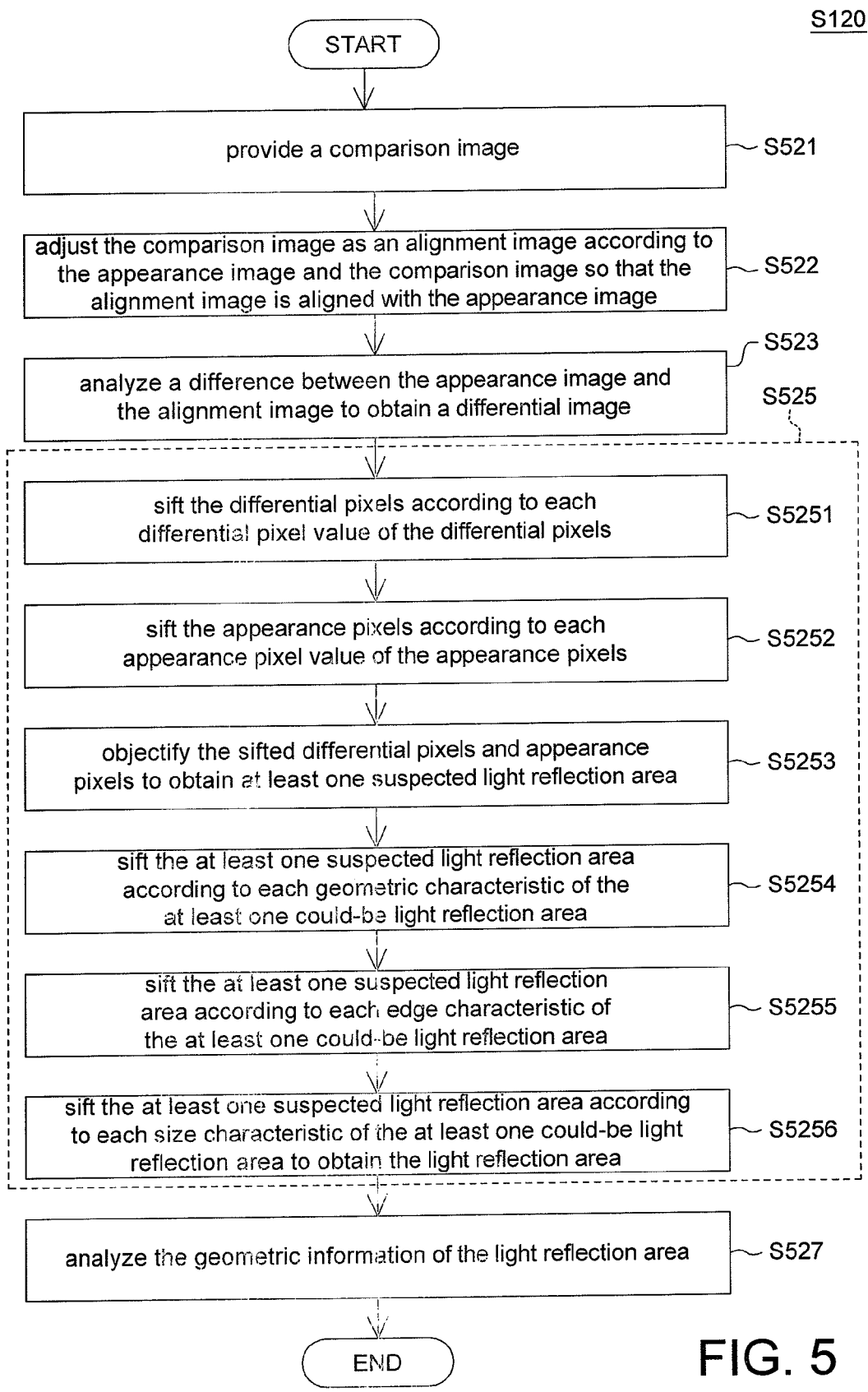
FIG. 5 shows a schematic diagram the step S120 of FIG. 2 according to another embodiment of the disclosure.
Figure 6:
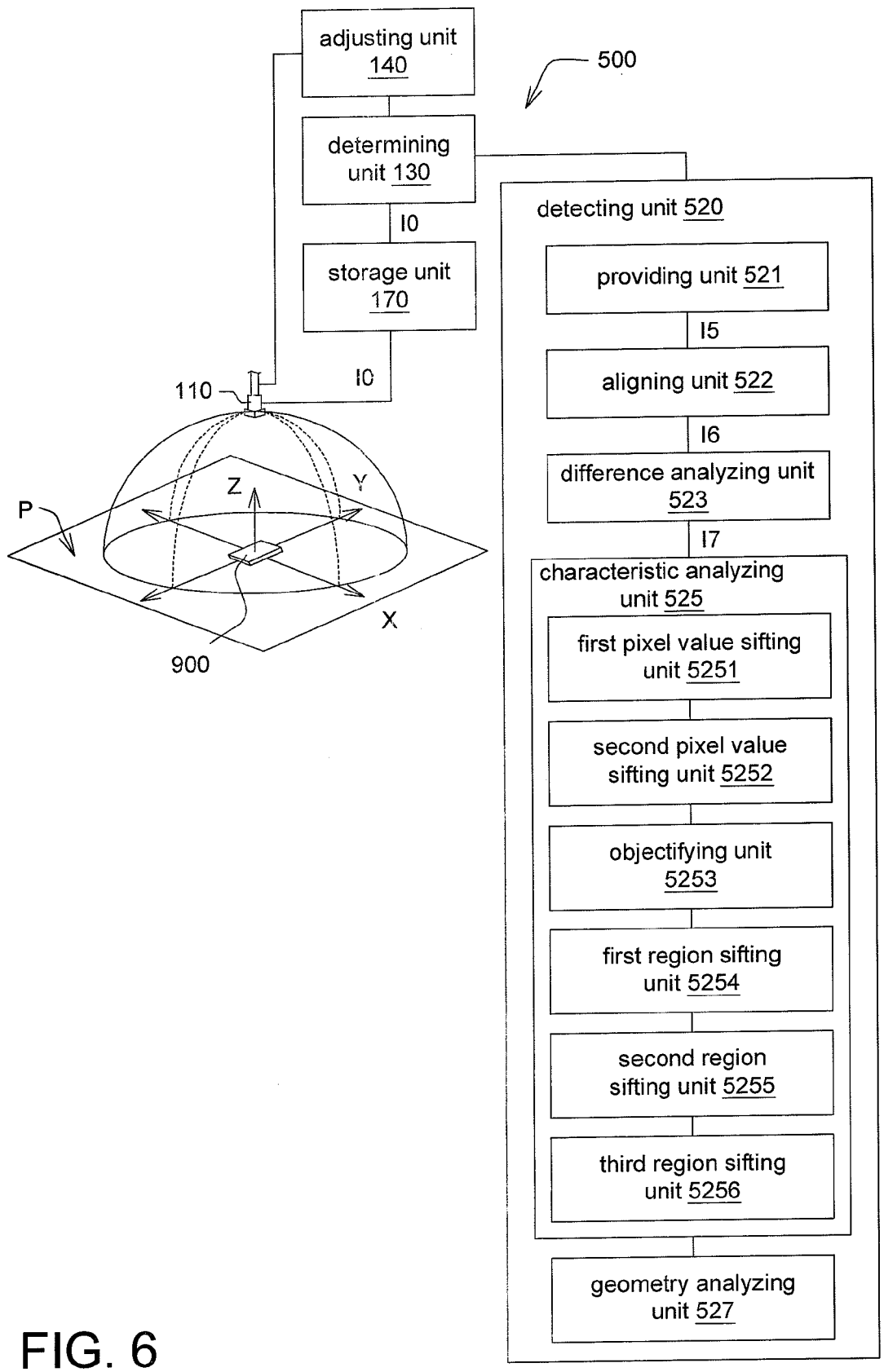
FIG. 6 shows a schematic diagram of a capturing system according to another embodiment of the disclosure.

The above step S120 can be implemented by steps S121 to S125 and S127 of FIG. 4 or other process. Referring to FIG. 5, a schematic diagram the step S120 of FIG. 2 according to another embodiment of the disclosure is shown. In an embodiment, step S120 can be implemented through a plurality of sub-steps S521 to S523, S525 and S527. Let another capturing system 500 of FIG. 6 be taken for example. A detecting unit 520 of the capturing system 500 includes a providing unit 521, an aligning unit 522, a difference analyzing unit 523, a characteristic analyzing unit 525 and a geometry analyzing unit 527. The characteristic analyzing unit 525 includes a first pixel sifting unit 5251, a second pixel sifting unit 5252, an objectifying unit 5253, a first region sifting unit 5254, a second region sifting unit 5255 and, a third region sifting unit 5256.

In step S521, a comparison image I5 is provided by the providing unit 521. The comparison image I5 is such as the object image previously captured by the image capturing unit 110.

In step S522, the comparison image I5 is adjusted as an alignment image I6 by the aligning unit 522 according to the appearance image I0 and the comparison image I5, so that the alignment image I6 is aligned with the appearance image I0. During the adjustment process, adjustment operations such as shifting, enlargement, reduction and rotation are performed on the comparison image I5, so that the pattern of the alignment image I6 corresponds to the pattern of the appearance image I0.

In step S523, a difference between the appearance image I0 and the alignment image I6 is analyzed by the difference analyzing unit 523 to obtain a differential image I7.

In step S525, the light reflection area is obtained by the characteristic analyzing unit 525 according to differential image I7 and the appearance image I0. In step S525, the differential image I7 includes a plurality of differential pixels. Through steps S5251 to 5256, the light reflection area is analyzed according to the differential pixels.

In step S5251, differential pixels are sifted by the first pixel sifting unit 5251 according to each differential pixel value of the differential pixels of the differential image I7. For example, the first pixel sifting unit 5251 deletes these differential pixels whose pixel values are smaller than a predetermined threshold but reserves these differential pixels whose pixel values are larger than the threshold. The reserved differential pixels are suspected reflective pixels.

In step S5252, the appearance pixels are sifted by the second pixel sifting unit 5252 according to each pixel value of the appearance pixels of the appearance image I0. For example, the second pixel sifting unit 5252 deletes these appearance pixels whose pixel values are smaller than a predetermined threshold but selects these appearance pixels whose pixel values are larger than the threshold. The selected appearance pixels are suspected reflective pixels.

In step S5253, the selected differential pixels and appearance pixels are objectified by the objectifying unit 5253 to obtain at least one suspected light reflection area. That is, the objectifying unit 5253 connects the selected differential pixels and appearance pixels to form a plurality of suspected light reflection areas one by one.

In step S5254, the suspected light reflection areas are sifted by the first region sifting unit 5254 according to the geometric characteristic of the suspected light reflection area. That is, the first region sifting unit 5254 deletes these suspected light reflection areas whose geometric characteristic is significant (the suspected light reflection areas with significant geometric characteristic could be the original pattern of the object 900) but reserves these suspected light reflection areas whose geometric characteristic is insignificant.

In step S5255, the suspected light reflection areas are sifted by the second region sifting unit 5255 according to the edge characteristic of the suspected light reflection area. That is, the second region sifting unit 5255 deletes these suspected light reflection areas whose edge fuzzy degree is lower (the suspected light reflection areas with lower edge fuzzy degree could be the original pattern of the object 900) but reserves these suspected light reflection areas whose edge fuzzy degree is higher. In the present step, the edge fuzzy degree is analyzed according to the pixel values of the original appearance image I0.

In step S5256, the suspected light reflection areas are sifted by the third region sifting unit 5256 according to the dimension characteristic of the suspected light reflection area to obtain the light reflection area. That is, these light reflection areas whose dimension characteristic is larger than a specific threshold can be set by the user or selected from the suspected light reflection areas built in the system, and can be defined as the light reflection areas.

In FIG. 5, steps S5254 to S5256 are performed in sequence. In other embodiments, steps S5254 to S5256 can be performed according to other arrangements of sequence, or, only one or two of steps S5254 to S5256 is performed. The number and sequence of steps S5254 to S5256 are determined according to the needs of the design.

In step S527, the dimension characteristic of the light reflection area, such as the center-of-gravity position or the geometric center position, are analyzed by the geometry analyzing unit 527. The dimension characteristic obtained from analysis can be used in step S130 or step S150.

According to the above embodiments of the present disclosure, the dimension characteristic of the light reflection area of the appearance image captured at each view-angle is reduced through dynamic detection and adjustment. When performing surface quality testing, the object image captured according to the above capturing method is less affected by the light reflection area. Furthermore, through proactive detection and adjustment, the influence produced by the light reflection area is effectively reduced, and the object does not require specific light source, so that the hardware cost can thus be reduced accordingly.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A capturing method for a plurality of images with different view-angles, wherein the method comprises:
    capturing an appearance image of an object as a current appearance image by an image capturing unit at a capturing angle;
    detecting a light reflection area of the appearance image by a detecting unit, and analyzing a dimension characteristic of the light reflection area by the same;
    determining whether the dimension characteristic of the light reflection area is larger than a first predetermined value;
    adjusting the capturing angle within a first adjusting range if the dimension characteristic of the light reflection area is larger than the first predetermined value;
    wherein, after the step of adjusting the capturing angle within a first adjusting range is performed, the step of capturing the appearance image is performed again; and
    storing the current appearance image and adjusting the capturing angle within a second adjusting range if the dimension characteristic of the light reflection area is not larger than the first predetermined value;
    further performing the step of capturing the appearance image again after the step of adjusting the capturing angle within the second adjusting range is completed.

2. The capturing method for the images with different view-angles according to claim 1, wherein the dimension characteristic is a ratio of an area measurement, a perimeter, each length of a long axis and a short axis, or a ratio of the long axis to the short axis.

3. The capturing method for the images with different view-angles according to claim 1, wherein the second adjusting range is larger than the first adjusting range.

4. The capturing method for the images with different view-angles according to claim 1, wherein the second adjusting range is smaller than the first adjusting range.

5. The capturing method for the images with different view-angles according to claim 1, further comprising:
    determining whether the dimension characteristic of the light reflection area is larger than a second predetermined value if the dimension characteristic of the light reflection area is not larger than the first predetermined value;

adjusting an environment brightness if the dimension characteristic of the light reflection area is larger than the second predetermined value;

wherein, after the step of adjusting the environment brightness is completed, the step of capturing the appearance image is further performed again.

6. The capturing method for the images with different view-angles according to claim 5, further comprising:

storing the current appearance image and adjusting the capturing angle within a second adjusting range if the dimension characteristic of the light reflection area is not larger than the second predetermined value, which is larger than the first adjusting range;

further performing the step of capturing the appearance image again after the step of adjusting the capturing angle within the second adjusting range is completed.

7. The capturing method for the images with different view-angles according to claim 1, wherein the step of detecting the light reflection area by the detecting unit and analyzing the dimension characteristic of the light reflection area by the same comprises:

performing a log transform process on the appearance image to obtain a log image;

performing a Gaussian filtering process on the log image to obtain a filtered image;

performing an exponential transform process on the filtered image to obtain an exponential image;

analyzing a difference between the appearance image and the exponential image to obtain a residual image;

obtaining the light reflection area according to the residual image; and analyzing the dimension characteristic of the light reflection area.

8. The capturing method for the images with different view-angles according to claim 7, wherein the residual image comprises a plurality of residual pixels, and the step of obtaining the light reflection area according to the residual image comprises:

sifting the residual pixels according to each residual pixel value of the residual pixels;

objectifying the sifted residual pixels to obtain at least one suspected light reflection area; and sifting the at least one suspected light reflection area according to each geometric characteristic, each edge characteristic or each size characteristic of the at least one suspected light reflection area to obtain the light reflection area.

9. The capturing method for the images with different view-angles according to claim 1, wherein the step of detecting the light reflection area by the detecting unit and analyzing the dimension characteristic of the light reflection area by the same comprises:

providing a comparison image;

adjusting the comparison image as an alignment image according to the appearance image and the comparison image so that the alignment image is aligned with the appearance image;

analyzing a difference between the appearance image and the alignment image to obtain a differential image;

obtaining the light reflection area according to the differential image and the appearance image; and analyzing the dimension characteristic of the light reflection area.

10. The capturing method for the images with different view-angles according to claim 9, wherein the differential image comprises a plurality of differential pixels, the appearance image comprises a plurality of appearance pixels, and the step of obtaining the light reflection area according to the differential image and the appearance image comprises:

sifting the differential pixels according to each differential pixel value of the differential pixels;

sifting the appearance pixels according to each appearance pixel value of the appearance pixels;

objectifying the sifted differential pixels and the appearance pixels to obtain at least one suspected light reflection area; and sifting the at least one suspected light reflection area according to each geometric characteristic, each edge characteristic or each size characteristic of the at least one suspected light reflection area to obtain the light reflection area.

11. A capturing system for capturing a plurality of images with different view-angles, comprising:

an image capturing unit used for capturing an appearance image of an object as a current appearance image at a capturing angle;

a detecting unit used for detecting a light reflection area of the appearance image and analyzing a dimension characteristic of the light reflection area;

a determining unit used for determining whether the dimension characteristic of the light reflection area is larger than a first predetermined value;

an adjusting unit used for adjusting the capturing angle within a first adjusting range if the dimension characteristic of the light reflection area is larger than the first predetermined value;

wherein, after the adjusting unit adjusts the capturing angle within a first adjusting range, the image capturing unit again captures the appearance image; and a storage unit used for storing the current appearance image if the dimension characteristic of the light reflection area is not larger than the first predetermined value, wherein the adjusting unit adjusts the capturing angle within a second adjusting range which is larger than the first adjusting range, and after the adjusting unit adjusts the capturing angle within the second adjusting range, the image capturing unit again captures the appearance image.

12. The capturing system according to claim 11, wherein if the dimension characteristic of the light reflection area is not larger than the first predetermined value, then the determining unit further determines whether the dimension characteristic of the light reflection area is larger than a second predetermined value;

if the dimension characteristic of the light reflection area is larger than the second predetermined value, then the adjusting unit adjusts an environment brightness;

after the adjusting unit adjusts the environment brightness, the image capturing unit again captures the appearance image.

13. The capturing system according to claim 12, wherein the storage unit used for storing the current appearance image if the dimension characteristic of the light reflection area is not larger than the second predetermined value, wherein the adjusting unit adjusts the capturing angle within a second adjusting range, and after the adjusting unit adjusts the capturing angle within the second adjusting range, the image capturing unit again captures the appearance image.

14. The capturing system according to claim 13, wherein the second adjusting range is larger than the first adjusting range.

15. The capturing system according to claim 13, wherein the second adjusting range is smaller than the first adjusting range.

16. The capturing system according to claim 11, wherein the detecting unit comprises:
- a log transform unit used for performing a log transform process on the appearance image to obtain a log image;
- a Gaussian filtering unit used for performing a Gaussian filtering process on the log image to obtain a filtered image;
- an exponential transform unit used for performing an exponential transform process on the filtered image to obtain an exponential image;
- a difference analyzing unit used for analyzing a difference between the appearance image and the exponential image to obtain a residual image;
- a characteristic analyzing unit used for obtaining the light reflection area according to the residual image; and
- a geometry analyzing unit used for analyzing the dimension characteristic of the light reflection area.

17. The capturing system according to claim 16, wherein the residual image comprises a plurality of residual pixels, and the characteristic analyzing unit comprises:
- a pixel sifting unit used for sifting the residual pixels according to each residual pixel value of the residual pixels;
- an objectifying unit used for objectifying the sifted residual pixels to obtain at least one suspected light reflection area; and
- a region sifting unit used for sifting one of the suspected light reflection area according to each geometric characteristic, each edge characteristic or each size characteristic of the at least one suspected light reflection area to obtain the light reflection area.

18. The capturing system according to claim 11, wherein the detecting unit comprises:
- a providing unit used for providing a comparison image;
- an aligning unit used for adjusting the comparison image as an alignment image according to the appearance image and the comparison image so that the alignment image is aligned with the appearance image;
- a difference analyzing unit used for analyzing a difference between the appearance image and the alignment image to obtain a differential image;
- a characteristic analyzing unit used for obtaining the light reflection area according to the differential image and the appearance image; and
- a geometry analyzing unit used for analyzing the dimension characteristic of the light reflection area.

19. The capturing system according to claim 18, wherein the differential image comprises a plurality of differential pixels, the appearance image comprises a plurality of appearance pixels, and the characteristic analyzing unit comprises:
- a pixel sifting unit used for sifting the differential pixels according to each differential pixel value of the differential pixels and sifting the appearance pixels according to each appearance pixel value of the appearance pixels;
- an objectifying unit used for objectifying the sifted differential pixels and the appearance pixels to obtain at least one suspected light reflection area; and
- a region sifting unit used for sifting one of the at least one suspected light reflection area according to each geometric characteristic, each edge characteristic or each size characteristic of the at least one suspected light reflection area to obtain the light reflection area.

* * * * *